United States Patent
Arnst et al.

(10) Patent No.: US 12,304,888 B2
(45) Date of Patent: May 20, 2025

(54) STABILIZER ADDITIVES FOR PLASTIC-DERIVED SYNTHETIC FEEDSTOCK

(71) Applicant: ECOLAB USA INC., St. Paul, MN (US)

(72) Inventors: Theodore C. Arnst, Sugar Land, TX (US); Karina Eureste, Iowa Colony, TX (US); Kameswara Vyakaranam, Sugar Land, TX (US); Jan Van Bauwel, Oelegem (BE); Ashish Dhawan, Aurora, IL (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 17/691,939

(22) Filed: Mar. 10, 2022

(65) Prior Publication Data
US 2022/0289648 A1 Sep. 15, 2022

Related U.S. Application Data

(60) Provisional application No. 63/159,266, filed on Mar. 10, 2021.

(51) Int. Cl.
*C07C 7/20* (2006.01)
*C07C 4/04* (2006.01)
(Continued)

(52) U.S. Cl.
CPC ............... *C07C 7/20* (2013.01); *C07C 4/04* (2013.01); *C07C 4/22* (2013.01); *C08J 11/12* (2013.01)

(58) Field of Classification Search
CPC ..... C07C 7/20; C07C 4/04; C07C 4/22; C08J 11/12; C10L 9/00; C10L 2290/02;
(Continued)

(56) References Cited

U.S. PATENT DOCUMENTS 3,093,623 A    6/1963   Ilnyckyj et al.
3,819,589 A    6/1974   Fauke et al.
(Continued)

FOREIGN PATENT DOCUMENTS

AU    2005227358 A1    7/2006
AU    2013263852 A1    8/2014
(Continued)

OTHER PUBLICATIONS

Vasile, Cornelia et al. "Feedstock recycling from plastic and thermoset fractions of used computers (I): pyrolysis," Journal of Material Cycles and Waste Management (2006) 8, pp. 99-108.
(Continued)

*Primary Examiner* — Thuan D Dang
(74) *Attorney, Agent, or Firm* — Eric D. Babych; Barnes & Thornburg LLP

(57) ABSTRACT

Disclosed are antioxidants used in compositions and methods to stabilize synthetic feedstock derived from plastic. Some methods disclosed herein include adding an antioxidant composition to a plastic-derived synthetic feedstock composition. Some methods disclosed herein include heating plastic under substantially oxygen free conditions at a temperature of from about 400° C. to about 800° C. to produce a pyrolysis effluent, distilling the pyrolysis effluent, recovering the synthetic feedstock, and adding a stabilizer to the synthetic feedstock to reduce contamination. The disclosure also provides compositions including a synthetic feedstock derived from plastic and an antioxidant.

8 Claims, 3 Drawing Sheets

(51) Int. Cl.
*C07C 4/22* (2006.01)
*C08J 11/12* (2006.01)

(58) Field of Classification Search
CPC ............. C10L 2290/38; C10L 2290/54; C10L 2290/541; C10L 2290/543; C10L 5/46; C10G 1/02; C10G 1/10
See application file for complete search history.

(56) References Cited

U.S. PATENT DOCUMENTS

| | | | |
|---|---|---|---|
| 3,901,951 A | 8/1975 | Nishizaki |
| 3,947,368 A | 3/1976 | Sweeney |
| 4,030,984 A | 6/1977 | Chambers |
| 4,108,730 A | 8/1978 | Chen et al. |
| 4,118,281 A | 10/1978 | Yan |
| 4,121,026 A | 10/1978 | Cheng et al. |
| 4,175,211 A | 11/1979 | Chen et al. |
| 4,210,491 A | 7/1980 | Schulman |
| 4,211,534 A | 7/1980 | Feldman |
| 4,235,675 A | 11/1980 | Bechthold |
| 4,235,676 A | 11/1980 | Chambers |
| 4,252,542 A | 2/1981 | Spence |
| 4,731,095 A | 3/1988 | Garapon et al. |
| 4,732,092 A | 3/1988 | Gould |
| 4,874,395 A | 10/1989 | Meyer |
| 4,900,331 A | 2/1990 | Le |
| 4,900,332 A | 2/1990 | Denis et al. |
| 4,941,952 A | 7/1990 | Betz |
| 4,948,495 A | 8/1990 | Coburn |
| 4,970,969 A | 11/1990 | Koptis et al. |
| 4,983,278 A | 1/1991 | Cha et al. |
| 5,167,772 A | 12/1992 | Parker, Sr. |
| 5,182,036 A | 1/1993 | Okorodudu et al. |
| 5,214,224 A | 5/1993 | Comer et al. |
| 5,316,734 A | 5/1994 | Yamaguchi |
| 5,425,789 A | 6/1995 | Lewtas et al. |
| 5,441,545 A | 8/1995 | Lewtas et al. |
| 5,464,876 A | 11/1995 | Lyding et al. |
| 5,468,780 A | 11/1995 | Kubota et al. |
| 5,509,944 A | 4/1996 | Venkatadri et al. |
| 5,707,943 A | 1/1998 | Covitch |
| 5,711,767 A | 1/1998 | Gande et al. |
| 5,720,232 A | 2/1998 | Meador |
| 5,851,429 A | 12/1998 | Magyar |
| 5,894,012 A | 4/1999 | Denison |
| 6,036,124 A | 3/2000 | Takahashi et al. |
| 6,143,043 A | 11/2000 | Botros |
| 6,149,881 A | 11/2000 | Hanson et al. |
| 6,150,577 A | 11/2000 | Miller et al. |
| 6,187,083 B1 | 2/2001 | Malhotra et al. |
| 6,774,271 B2 | 8/2004 | Jiang |
| 6,774,272 B2 | 8/2004 | Miller |
| 6,822,126 B2 | 11/2004 | Miller |
| 6,830,597 B1 | 12/2004 | Green |
| 7,041,738 B2 | 5/2006 | Krull et al. |
| 7,413,583 B2 | 8/2008 | Langer et al. |
| 7,534,748 B2 | 5/2009 | Patel et al. |
| 7,820,604 B2 | 10/2010 | Ruhe, Jr. et al. |
| 7,820,605 B2 | 10/2010 | Stokes et al. |
| 8,048,333 B2 | 11/2011 | Vitale et al. |
| 8,088,961 B2 | 1/2012 | Miller |
| 8,158,842 B2 | 4/2012 | McCall |
| 8,304,592 B2 | 11/2012 | Luebke |
| 8,329,969 B2 | 12/2012 | McCall et al. |
| 8,394,264 B2 | 3/2013 | Sappok et al. |
| 8,425,627 B2 | 4/2013 | Dietz et al. |
| 8,466,332 B1 | 6/2013 | Hemmings et al. |
| 8,703,674 B2 | 4/2014 | Umehara et al. |
| 8,722,596 B2 | 5/2014 | Umehara et al. |
| 8,927,797 B2 | 1/2015 | Sarker |
| 8,992,636 B1 | 3/2015 | Fang et al. |
| 9,012,385 B2 | 4/2015 | Di Biase et al. |
| 9,175,141 B2 | 11/2015 | Wray et al. |
| 9,181,510 B2 | 11/2015 | Barton et al. |
| 9,200,207 B2 | 12/2015 | Huang et al. |
| 9,234,138 B1 | 1/2016 | Li et al. |
| 9,315,732 B1 | 4/2016 | Fowler |
| 9,534,183 B2 | 1/2017 | Papin et al. |
| 9,556,395 B2 | 1/2017 | Kashani-Shirazi et al. |
| 9,624,439 B2 | 4/2017 | Bakaya et al. |
| 10,131,847 B2 | 11/2018 | McNamara et al. |
| 10,150,928 B2 | 12/2018 | Scherer et al. |
| 10,160,927 B2 | 12/2018 | Hellawell et al. |
| 10,208,253 B2 | 2/2019 | McNamara et al. |
| 10,233,395 B2 | 3/2019 | Ward et al. |
| 2002/0040546 A1 | 4/2002 | Botros |
| 2003/0031722 A1 | 2/2003 | Cao et al. |
| 2003/0047437 A1 | 3/2003 | Stankevitch |
| 2003/0050519 A1 | 3/2003 | Cheng |
| 2003/0104943 A1 | 6/2003 | Lennon et al. |
| 2003/0166811 A1 | 9/2003 | Peiffer et al. |
| 2004/0152930 A1* | 8/2004 | O'Rear ............... C10L 1/2222 585/1 |
| 2004/0192980 A1 | 9/2004 | Appel et al. |
| 2004/0204620 A1 | 10/2004 | Grispin |
| 2005/0050792 A1 | 3/2005 | Corkwell et al. |
| 2005/0086855 A1 | 4/2005 | Tack et al. |
| 2005/0131260 A1 | 6/2005 | Tokarz |
| 2006/0037852 A1 | 2/2006 | Noto |
| 2007/0051033 A1 | 3/2007 | Martin et al. |
| 2007/0161519 A1 | 6/2007 | Cravey et al. |
| 2007/0173419 A1 | 7/2007 | Mead et al. |
| 2008/0051520 A1 | 2/2008 | Srinivasan et al. |
| 2008/0103076 A1 | 5/2008 | Ruhe et al. |
| 2008/0178522 A1 | 7/2008 | Siggelkow et al. |
| 2008/0200738 A1 | 8/2008 | Grispin |
| 2008/0295397 A1 | 12/2008 | Muth |
| 2009/0170739 A1 | 7/2009 | Miller |
| 2010/0065411 A1 | 3/2010 | Li et al. |
| 2010/0180492 A1 | 7/2010 | Krull et al. |
| 2010/0320070 A1 | 12/2010 | DeWhitt |
| 2011/0042268 A1 | 2/2011 | Stark et al. |
| 2011/0083953 A1 | 4/2011 | Horn et al. |
| 2011/0306808 A1 | 12/2011 | Appel et al. |
| 2012/0215043 A1 | 8/2012 | Gaffney |
| 2012/0220675 A1 | 8/2012 | DeWhitt |
| 2012/0245063 A1 | 9/2012 | DiBiase et al. |
| 2012/0255222 A1 | 10/2012 | DiBiase et al. |
| 2012/0261247 A1 | 10/2012 | McNamara et al. |
| 2012/0264662 A1 | 10/2012 | DiBiase et al. |
| 2012/0264664 A1 | 10/2012 | DiBiase et al. |
| 2012/0277133 A1 | 11/2012 | DiBiase et al. |
| 2012/0283156 A1 | 11/2012 | DiBiase et al. |
| 2013/0015608 A1 | 1/2013 | Hamby et al. |
| 2013/0025189 A1 | 1/2013 | Burgazli et al. |
| 2013/0225462 A1 | 8/2013 | DiBiase et al. |
| 2013/0227878 A1 | 9/2013 | Wolf et al. |
| 2014/0054815 A1 | 2/2014 | Houk et al. |
| 2014/0190692 A1 | 7/2014 | Hibbeler et al. |
| 2014/0259923 A1 | 9/2014 | Blair |
| 2014/0262728 A1 | 9/2014 | Karanikas |
| 2014/0338253 A1 | 11/2014 | Jung et al. |
| 2015/0060258 A1 | 3/2015 | Appel et al. |
| 2015/0113859 A1 | 4/2015 | Voelkel et al. |
| 2015/0113867 A1 | 4/2015 | Voelkel et al. |
| 2015/0139889 A1 | 5/2015 | Horn et al. |
| 2015/0197692 A1 | 7/2015 | Wang |
| 2015/0203784 A1 | 7/2015 | Barton et al. |
| 2015/0232781 A1 | 8/2015 | Barton |
| 2015/0284495 A1 | 10/2015 | Reed et al. |
| 2016/0040073 A1 | 2/2016 | Bakaya et al. |
| 2016/0040089 A1 | 2/2016 | Baker et al. |
| 2016/0046880 A1 | 2/2016 | Combs |
| 2016/0115369 A1 | 4/2016 | Soriano, Jr. et al. |
| 2016/0169509 A1 | 6/2016 | Fowler |
| 2016/0257879 A1 | 9/2016 | Huang et al. |
| 2017/0015911 A1 | 1/2017 | Houk et al. |
| 2017/0081591 A1 | 3/2017 | Reed |
| 2017/0114279 A1 | 4/2017 | Alyaser |
| 2017/0130153 A1 | 5/2017 | Peretolchin et al. |
| 2017/0190949 A1 | 7/2017 | Solomon et al. |
| 2017/0218278 A1 | 8/2017 | Bakaya et al. |
| 2017/0321124 A1 | 11/2017 | Hsu et al. |

(56) References Cited

U.S. PATENT DOCUMENTS

| | | | |
|---|---|---|---|
| 2017/0349836 | A1 | 12/2017 | Duncan |
| 2018/0010048 | A1 | 1/2018 | Oluwaseun et al. |
| 2018/0010049 | A1 | 1/2018 | Tenore et al. |
| 2018/0010050 | A1* | 1/2018 | Van Der Ree ........... C10G 9/00 |
| 2018/0066200 | A1 | 3/2018 | Scherer |
| 2018/0086862 | A1 | 3/2018 | Kundu et al. |
| 2018/0244605 | A1 | 8/2018 | Khanlari et al. |
| 2018/0251692 | A1 | 9/2018 | Mezger et al. |
| 2019/0168192 | A1 | 6/2019 | Gaffney |
| 2019/0177652 | A1 | 6/2019 | Atkins et al. |
| 2019/0203135 | A1 | 7/2019 | Soriano, Jr. et al. |
| 2020/0017786 | A1 | 1/2020 | Li et al. |
| 2022/0081634 | A1 | 3/2022 | Arnst et al. |
| 2022/0396735 | A1 | 12/2022 | Wu et al. |

FOREIGN PATENT DOCUMENTS

| | | |
|---|---|---|
| BR | PI1004634 A2 | 3/2013 |
| BR | 102016027627 A2 | 6/2018 |
| CA | 2202941 | 10/1998 |
| CN | 1149598 A | 5/1997 |
| CN | 1239108 A | 12/1999 |
| CN | 1338341 A | 3/2002 |
| CN | 101172238 A | 5/2008 |
| CN | 101210173 A | 7/2008 |
| CN | 101235279 A | 8/2008 |
| CN | 101328414 A | 12/2008 |
| CN | 101386724 A | 3/2009 |
| CN | 201458375 U | 5/2010 |
| CN | 101831313 A | 9/2010 |
| CN | 201581050 U | 9/2010 |
| CN | 101886020 A | 11/2010 |
| CN | 201648314 U | 11/2010 |
| CN | 1962735 B | 12/2010 |
| CN | 101177502 B | 12/2010 |
| CN | 102504855 A | 6/2012 |
| CN | 202265543 U | 6/2012 |
| CN | 202415456 U | 9/2012 |
| CN | 202705307 U | 1/2013 |
| CN | 202725185 U | 2/2013 |
| CN | 202953992 U | 5/2013 |
| CN | 202953993 U | 5/2013 |
| CN | 203043985 U | 7/2013 |
| CN | 203048877 U | 7/2013 |
| CN | 103242872 A | 8/2013 |
| CN | 103305253 A | 9/2013 |
| CN | 103382398 A | 11/2013 |
| CN | 203269856 U | 11/2013 |
| CN | 103450912 A | 12/2013 |
| CN | 203319926 U | 12/2013 |
| CN | 203333590 U | 12/2013 |
| CN | 103571565 A | 2/2014 |
| CN | 203487095 U | 3/2014 |
| CN | 102942943 B | 4/2014 |
| CN | 104031665 A | 9/2014 |
| CN | 104073273 A | 10/2014 |
| CN | 104073279 A | 10/2014 |
| CN | 104130787 A | 11/2014 |
| CN | 104140827 A | 11/2014 |
| CN | 203960130 U | 11/2014 |
| CN | 204058363 U | 12/2014 |
| CN | 204211689 U | 3/2015 |
| CN | 204224524 U | 3/2015 |
| CN | 204281679 U | 4/2015 |
| CN | 103172934 B | 6/2015 |
| CN | 204417413 U | 6/2015 |
| CN | 204434552 U | 7/2015 |
| CN | 103275746 B | 8/2015 |
| CN | 204644272 U | 9/2015 |
| CN | 104974779 A | 10/2015 |
| CN | 103980925 B | 12/2015 |
| CN | 204939396 U | 1/2016 |
| CN | 104531199 B | 3/2016 |
| CN | 205088187 U | 3/2016 |
| CN | 105462660 A | 4/2016 |
| CN | 205223110 U | 5/2016 |
| CN | 105713641 B | 6/2016 |
| CN | 205347348 U | 6/2016 |
| CN | 105778955 A | 7/2016 |
| CN | 104560100 B | 8/2016 |
| CN | 205473591 U | 8/2016 |
| CN | 105925292 A | 9/2016 |
| CN | 205635485 U | 10/2016 |
| CN | 205653411 U | 10/2016 |
| CN | 106085473 A | 11/2016 |
| CN | 106185941 A | 12/2016 |
| CN | 106185943 A | 12/2016 |
| CN | 205774331 U | 12/2016 |
| CN | 106281384 A | 1/2017 |
| CN | 106318546 A | 1/2017 |
| CN | 106433724 A | 2/2017 |
| CN | 106433726 A | 2/2017 |
| CN | 106433732 A | 2/2017 |
| CN | 106544050 A | 3/2017 |
| CN | 106544051 A | 3/2017 |
| CN | 106698421 A | 5/2017 |
| CN | 104650943 B | 6/2017 |
| CN | 206308313 U | 7/2017 |
| CN | 206318947 U | 7/2017 |
| CN | 206318948 U | 7/2017 |
| CN | 107033941 A | 8/2017 |
| CN | 107057745 A | 8/2017 |
| CN | 206392023 U | 8/2017 |
| CN | 206408173 U | 8/2017 |
| CN | 107151559 A | 9/2017 |
| CN | 107163967 A | 9/2017 |
| CN | 107216888 A | 9/2017 |
| CN | 105733644 B | 10/2017 |
| CN | 107236568 A | 10/2017 |
| CN | 107267181 A | 10/2017 |
| CN | 107267182 A | 10/2017 |
| CN | 206545002 U | 10/2017 |
| CN | 107384447 A | 11/2017 |
| CN | 107384465 A | 11/2017 |
| CN | 107418603 A | 12/2017 |
| CN | 107418605 A | 12/2017 |
| CN | 107420912 A | 12/2017 |
| CN | 107433280 A | 12/2017 |
| CN | 107433281 A | 12/2017 |
| CN | 107433282 A | 12/2017 |
| CN | 107434977 A | 12/2017 |
| CN | 107446608 A | 12/2017 |
| CN | 107446610 A | 12/2017 |
| CN | 107523362 A | 12/2017 |
| CN | 206692598 U | 12/2017 |
| CN | 206720749 U | 12/2017 |
| CN | 107537847 A | 1/2018 |
| CN | 107641522 A | 1/2018 |
| CN | 107674695 A | 2/2018 |
| CN | 106118708 B | 3/2018 |
| CN | 107828438 A | 3/2018 |
| CN | 105462615 B | 4/2018 |
| CN | 207362144 U | 5/2018 |
| CN | 108117881 A | 6/2018 |
| CN | 207446192 U | 6/2018 |
| CN | 207537397 U | 6/2018 |
| CN | 105038829 B | 7/2018 |
| CN | 105779017 B | 7/2018 |
| CN | 105950200 B | 7/2018 |
| CN | 106635116 B | 7/2018 |
| CN | 108285800 A | 7/2018 |
| CN | 108299673 A | 7/2018 |
| CN | 105754628 B | 8/2018 |
| CN | 108384565 A | 8/2018 |
| CN | 108395572 A | 8/2018 |
| CN | 108410007 A | 8/2018 |
| CN | 108441241 A | 8/2018 |
| CN | 108467513 A | 8/2018 |
| CN | 106635114 B | 9/2018 |
| CN | 106753502 B | 9/2018 |
| CN | 108517222 A | 9/2018 |
| CN | 207845569 U | 9/2018 |
| CN | 207845574 U | 9/2018 |
| CN | 207952195 U | 10/2018 |

(56) References Cited

FOREIGN PATENT DOCUMENTS

| | | | |
|---|---|---|---|
| CN | 106513419 B | 11/2018 |
| CN | 108841405 A | 11/2018 |
| CN | 106338066 B | 12/2018 |
| CN | 106338067 B | 12/2018 |
| CN | 109181738 A | 1/2019 |
| CN | 109266375 A | 1/2019 |
| CN | 106185938 B | 2/2019 |
| CN | 106734060 B | 4/2019 |
| CN | 106433725 B | 5/2019 |
| CN | 109749757 A | 5/2019 |
| CN | 109776274 A | 5/2019 |
| CN | 108085044 B | 10/2019 |
| CN | 108441242 B | 4/2020 |
| CN | 112063403 A | 12/2020 |
| CN | 106433703 B | 1/2022 |
| CN | 107057738 B | 8/2023 |
| DE | 2725650 A1 | 12/1977 |
| DE | 2748510 A1 | 5/1978 |
| DE | 2917293 A1 | 10/1980 |
| DE | 3030593 A1 | 3/1982 |
| DE | 3205603 A1 | 11/1982 |
| DE | 3323161 A1 | 1/1985 |
| DE | 4103738 A1 | 10/1991 |
| DE | 4210237 C2 | 2/1994 |
| DE | 4234385 A1 | 4/1994 |
| DE | 4329458 A1 | 3/1995 |
| DE | 4446964 A1 | 6/1995 |
| DE | 4403128 A1 | 8/1995 |
| DE | 4417721 A1 | 11/1995 |
| DE | 4423394 C1 | 3/1996 |
| DE | 4435238 A1 | 4/1996 |
| DE | 4437881 A1 | 4/1996 |
| DE | 19505544 C1 | 5/1996 |
| DE | 19617450 A1 | 11/1997 |
| DE | 19800567 A1 | 7/1999 |
| DE | 19834596 C1 | 2/2000 |
| DE | 202006003429 U1 | 8/2007 |
| DE | 202006003430 U1 | 8/2007 |
| DE | 102006014457 A1 | 10/2007 |
| DE | 102008019237 A1 | 11/2008 |
| DE | 102007051373 A1 | 4/2009 |
| DE | 102007054343 A1 | 5/2009 |
| DE | 102012204648 A1 | 9/2013 |
| DE | 102012008457 A1 | 10/2013 |
| DE | 102012109874 A1 | 4/2014 |
| DE | 102014014816 A1 | 4/2016 |
| EP | 0072387 A2 | 2/1983 |
| EP | 0191967 A2 | 8/1986 |
| EP | 0226895 A2 | 7/1987 |
| EP | 0297420 A2 | 1/1989 |
| EP | 0316827 A1 | 5/1989 |
| EP | 0391735 A1 | 10/1990 |
| EP | 0410889 A1 | 1/1991 |
| EP | 0659867 A2 | 6/1995 |
| EP | 0713906 A1 | 5/1996 |
| EP | 0890629 A1 | 1/1999 |
| EP | 0949321 A2 | 10/1999 |
| EP | 0693527 B1 | 6/2001 |
| EP | 1302526 A1 | 4/2003 |
| EP | 1380635 A2 | 1/2004 |
| EP | 1577366 A2 | 9/2005 |
| EP | 1686141 A2 | 8/2006 |
| EP | 1905811 A2 | 4/2008 |
| EP | 2878649 A1 | 6/2015 |
| EP | 2942382 A1 | 11/2015 |
| EP | 1577367 B1 | 3/2016 |
| EP | 2783764 B1 | 7/2016 |
| EP | 3085757 A1 | 10/2016 |
| EP | 3260181 A1 | 12/2017 |
| EP | 3421576 B1 | 3/2020 |
| FR | 2178061 A1 | 11/1973 |
| GB | 1525114 A | 9/1978 |
| GB | 2303859 A | 3/1997 |
| GB | 2434372 A | 7/2007 |
| GB | 2503065 A | 12/2013 |
| GB | 2515560 B | 12/2016 |
| GB | 2539518 B | 9/2017 |
| GB | 2570019 B | 4/2021 |
| JP | S511268 B2 | 1/1976 |
| JP | S5187584 A | 7/1976 |
| JP | S52144074 U | 11/1977 |
| JP | S5345302 A | 4/1978 |
| JP | S5424981 A | 2/1979 |
| JP | S5798591 U | 6/1982 |
| JP | S5971395 A | 4/1984 |
| JP | S6090293 A | 5/1985 |
| JP | S61123837 A | 6/1986 |
| JP | S62236893 A | 10/1987 |
| JP | S63260981 A | 10/1988 |
| JP | H01115918 A | 5/1989 |
| JP | H0397788 A | 4/1991 |
| JP | H03243692 A | 10/1991 |
| JP | H05100427 A | 4/1993 |
| JP | H05171159 A | 7/1993 |
| JP | H05320658 A | 12/1993 |
| JP | H06134434 A | 5/1994 |
| JP | H06158062 A | 6/1994 |
| JP | H06166880 A | 6/1994 |
| JP | H0948982 A | 2/1997 |
| JP | H0948983 A | 2/1997 |
| JP | H0995676 A | 4/1997 |
| JP | H09169982 A | 6/1997 |
| JP | H09310075 A | 12/1997 |
| JP | H1059704 A | 3/1998 |
| JP | H10110174 A | 4/1998 |
| JP | H10121056 A | 5/1998 |
| JP | H10279950 A | 10/1998 |
| JP | H10298569 A | 11/1998 |
| JP | H10330761 A | 12/1998 |
| JP | H10338886 A | 12/1998 |
| JP | H11166184 A | 6/1999 |
| JP | H11286686 A | 10/1999 |
| JP | H11286687 A | 10/1999 |
| JP | 2000086224 A | 3/2000 |
| JP | 2000191766 A | 7/2000 |
| JP | 2000239233 A | 9/2000 |
| JP | 2000265172 A | 9/2000 |
| JP | 2000290661 A | 10/2000 |
| JP | 2000309781 A | 11/2000 |
| JP | 2000355690 A | 12/2000 |
| JP | 2001049263 A | 2/2001 |
| JP | 2001115163 A | 4/2001 |
| JP | 2001187406 A | 7/2001 |
| JP | 2001200268 A | 7/2001 |
| JP | 2001232634 A | 8/2001 |
| JP | 2001232637 A | 8/2001 |
| JP | 2001240406 A | 9/2001 |
| JP | 2002020535 A | 1/2002 |
| JP | 2002047493 A | 2/2002 |
| JP | 2002053869 A | 2/2002 |
| JP | 2002138286 A | 5/2002 |
| JP | 2002285165 A | 10/2002 |
| JP | 2002327182 A | 11/2002 |
| JP | 2002332380 A | 11/2002 |
| JP | 2003039056 A | 2/2003 |
| JP | 2003041265 A | 2/2003 |
| JP | 3383296 B1 | 3/2003 |
| JP | 2003130319 A | 5/2003 |
| JP | 2003176483 A | 6/2003 |
| JP | 2003205281 A | 7/2003 |
| JP | 2003213034 A | 7/2003 |
| JP | 2003236517 A | 8/2003 |
| JP | 2003268098 A | 9/2003 |
| JP | 2004002054 A | 1/2004 |
| JP | 2004035807 A | 2/2004 |
| JP | 2004099693 A | 4/2004 |
| JP | 2004131358 A | 4/2004 |
| JP | 2004161971 A | 6/2004 |
| JP | 2004285134 A | 10/2004 |
| JP | 2004285255 A | 10/2004 |
| JP | 2004307779 A | 11/2004 |
| JP | 2004307780 A | 11/2004 |
| JP | 2005015701 A | 1/2005 |
| JP | 2005097737 A | 4/2005 |

(56) References Cited

FOREIGN PATENT DOCUMENTS

| | | |
|---|---|---|
| JP | 2005153434 A | 6/2005 |
| JP | 2005154510 A | 6/2005 |
| JP | 2005154516 A | 6/2005 |
| JP | 2005194537 A | 7/2005 |
| JP | 2005314552 A | 11/2005 |
| JP | 2005314748 A | 11/2005 |
| JP | 2006028593 A | 2/2006 |
| JP | 2006036688 A | 2/2006 |
| JP | 2006089742 A | 4/2006 |
| JP | 2006096979 A | 4/2006 |
| JP | 2006206810 A | 8/2006 |
| JP | 2006220328 A | 8/2006 |
| JP | 2006234291 A3 | 9/2006 |
| JP | 2007139363 A | 6/2007 |
| JP | 2008080634 A | 4/2008 |
| JP | 2008150477 A | 7/2008 |
| JP | 2010242071 A | 10/2010 |
| JP | 2011006528 A | 1/2011 |
| JP | 2011033333 A | 2/2011 |
| JP | 2011111511 A | 6/2011 |
| JP | 2011219622 A | 11/2011 |
| JP | 2011219627 A | 11/2011 |
| JP | 2011236098 A | 11/2011 |
| JP | 2011236099 A | 11/2011 |
| JP | 2011236377 A | 11/2011 |
| JP | 2012087222 A | 5/2012 |
| JP | 2012136672 A | 7/2012 |
| JP | 2013231109 A | 11/2013 |
| JP | 2014156544 A | 8/2014 |
| JP | 2018135443 A | 8/2018 |
| JP | 2019135278 A | 8/2019 |
| JP | 2019135281 A | 8/2019 |
| KR | 20100103953 A | 9/2010 |
| KR | 101156195 B1 | 6/2012 |
| KR | 101347906 B1 | 1/2014 |
| KR | 20140114614 A | 9/2014 |
| KR | 101815917 B1 | 1/2018 |
| KR | 101817728 B1 | 1/2018 |
| MX | 2011013990 A | 6/2012 |
| MX | 2015004252 A | 9/2016 |
| NL | 7303690 A | 9/1973 |
| PL | 401930 A1 | 6/2014 |
| RU | 16711 U1 | 2/2001 |
| RU | 2011151416 A | 6/2013 |
| SK | 28297 A3 | 4/1998 |
| TW | 261547 B | 11/1995 |
| WO | 198101713 A1 | 6/1981 |
| WO | 198700082 A1 | 1/1987 |
| WO | 198904355 A1 | 5/1989 |
| WO | 199111499 A1 | 8/1991 |
| WO | 199118960 A1 | 12/1991 |
| WO | 199201767 A1 | 2/1992 |
| WO | 199204423 A1 | 3/1992 |
| WO | 199209671 A1 | 6/1992 |
| WO | 199222528 A2 | 12/1992 |
| WO | 199410107 A1 | 5/1994 |
| WO | 199410507 A1 | 5/1994 |
| WO | 199413763 A1 | 6/1994 |
| WO | 199503375 A1 | 2/1995 |
| WO | 199532262 A1 | 11/1995 |
| WO | 199600268 A1 | 1/1996 |
| WO | 199612755 A1 | 5/1996 |
| WO | 199623104 A1 | 8/1996 |
| WO | 199701616 A1 | 1/1997 |
| WO | 199706224 A1 | 2/1997 |
| WO | 199844074 A1 | 10/1998 |
| WO | 199845239 A1 | 10/1998 |
| WO | 200006668 A1 | 2/2000 |
| WO | 2000047658 A1 | 8/2000 |
| WO | 200053385 A1 | 9/2000 |
| WO | 200053699 A1 | 9/2000 |
| WO | 200064998 A1 | 11/2000 |
| WO | 200103473 A1 | 1/2001 |
| WO | 2004018592 A1 | 3/2001 |
| WO | 200148032 A1 | 7/2001 |
| WO | 200160948 A1 | 8/2001 |
| WO | 2001062823 A1 | 8/2001 |
| WO | 2002022498 A1 | 3/2002 |
| WO | 200231082 A1 | 4/2002 |
| WO | 2002072731 A1 | 9/2002 |
| WO | 2003029384 A1 | 4/2003 |
| WO | 2003042337 A2 | 5/2003 |
| WO | 2003047778 A1 | 6/2003 |
| WO | 2004011165 A1 | 2/2004 |
| WO | 2004072208 A1 | 8/2004 |
| WO | 2004076595 A1 | 9/2004 |
| WO | 2005040316 A2 | 5/2005 |
| WO | 2005087897 A1 | 9/2005 |
| WO | 2005097448 A1 | 10/2005 |
| WO | 2005097953 A1 | 10/2005 |
| WO | 2005108525 A1 | 11/2005 |
| WO | 2005111093 A1 | 11/2005 |
| WO | 2005121278 A1 | 12/2005 |
| WO | 2006043924 A1 | 4/2006 |
| WO | 2006096085 A1 | 9/2006 |
| WO | 2006096086 A1 | 9/2006 |
| WO | 2006124793 A1 | 11/2006 |
| WO | 2007009022 A2 | 1/2007 |
| WO | 2007014489 A1 | 2/2007 |
| WO | 2007050746 A1 | 5/2007 |
| WO | 2007091146 A1 | 8/2007 |
| WO | 2007115443 A1 | 10/2007 |
| WO | 2007143673 A1 | 12/2007 |
| WO | 2008030137 A1 | 3/2008 |
| WO | 2008075105 A1 | 6/2008 |
| WO | 2008079054 A2 | 7/2008 |
| WO | 2008126040 A2 | 10/2008 |
| WO | 2009064685 A2 | 5/2009 |
| WO | 2009087080 A2 | 7/2009 |
| WO | 2009099341 A2 | 8/2009 |
| WO | 2010049824 A2 | 5/2010 |
| WO | 2010053381 A1 | 5/2010 |
| WO | 2010106538 A1 | 9/2010 |
| WO | 2010106539 A1 | 9/2010 |
| WO | 2010116211 A1 | 10/2010 |
| WO | 2010130404 A1 | 11/2010 |
| WO | 2011008074 A1 | 1/2011 |
| WO | 2011008075 A1 | 1/2011 |
| WO | 2011009419 A1 | 1/2011 |
| WO | 2011025593 A1 | 3/2011 |
| WO | 2011028515 A2 | 3/2011 |
| WO | 2011034446 A1 | 3/2011 |
| WO | 2011079894 A2 | 7/2011 |
| WO | 2011127701 A1 | 10/2011 |
| WO | 2011131793 A2 | 10/2011 |
| WO | 2012006523 A1 | 1/2012 |
| WO | 2012014478 A1 | 2/2012 |
| WO | 2012014480 A1 | 2/2012 |
| WO | 2012018403 A1 | 2/2012 |
| WO | 2012110991 A1 | 8/2012 |
| WO | 2012127085 A1 | 9/2012 |
| WO | 2012129482 A2 | 9/2012 |
| WO | 2012131485 A1 | 10/2012 |
| WO | 2012162837 A1 | 12/2012 |
| WO | 2012172527 A2 | 12/2012 |
| WO | 2013032027 A1 | 3/2013 |
| WO | 2013036151 A2 | 3/2013 |
| WO | 2013070801 A1 | 5/2013 |
| WO | 2013087701 A1 | 6/2013 |
| WO | 2013089587 A1 | 6/2013 |
| WO | 2013106546 A1 | 7/2013 |
| WO | 2013119941 A1 | 8/2013 |
| WO | 2013123377 A1 | 8/2013 |
| WO | 2013171510 A1 | 11/2013 |
| WO | 2013187788 A2 | 12/2013 |
| WO | 2014032843 A1 | 3/2014 |
| WO | 2014041212 A1 | 3/2014 |
| WO | 2014043051 A1 | 3/2014 |
| WO | 2014051514 A1 | 4/2014 |
| WO | 2014057430 A1 | 4/2014 |
| WO | 2014070908 A1 | 5/2014 |
| WO | 2014135754 A1 | 9/2014 |
| WO | 2014167139 A2 | 10/2014 |
| WO | 2014177727 A1 | 11/2014 |

(56) References Cited

FOREIGN PATENT DOCUMENTS

| | | |
|---|---|---|
| WO | 2014184290 A1 | 11/2014 |
| WO | 2014200330 A1 | 12/2014 |
| WO | 2015019313 A2 | 2/2015 |
| WO | 2015082755 A2 | 6/2015 |
| WO | 2015162505 A2 | 10/2015 |
| WO | 2015194978 A1 | 12/2015 |
| WO | 2016030460 A1 | 3/2016 |
| WO | 2016034739 A1 | 3/2016 |
| WO | 2016187144 A1 | 11/2016 |
| WO | 2016209194 A1 | 12/2016 |
| WO | 2017009208 A1 | 1/2017 |
| WO | 2017060464 A1 | 4/2017 |
| WO | 2017088015 A1 | 6/2017 |
| WO | 2017113020 A1 | 7/2017 |
| WO | 2017115261 A1 | 7/2017 |
| WO | 2017152205 A1 | 9/2017 |
| WO | 2017168164 A1 | 10/2017 |
| WO | 2017172351 A2 | 10/2017 |
| WO | 2017173006 A2 | 10/2017 |
| WO | 2017198896 A1 | 11/2017 |
| WO | 2017205275 A1 | 11/2017 |
| WO | 2018000050 A1 | 1/2018 |
| WO | 2018084330 A1 | 5/2018 |
| WO | 2018085934 A1 | 5/2018 |
| WO | 2018104443 A1 | 6/2018 |
| WO | 2020178597 A1 | 9/2020 |
| WO | 2020178599 A1 | 9/2020 |
| WO | 2020212315 A1 | 10/2020 |
| WO | 2022192577 A1 | 9/2022 |
| WO | 2022212502 A1 | 10/2022 |

OTHER PUBLICATIONS

Vouvoudi, Evangelia C. et al. "Pyrolytic degradation of common polymers present in packaging materials," Journal of Thermal Analysis and Calorimetry (2019) 138, pp. 2683-2689.

Williams, P.T. et al. "Recycling plastic waste by pyrolysis," Journal of the Institute of Energy (1998) 71, pp. 81-93.

Williams, Paul T. "Yield and Composition of Gases and Oils/Waxes from the Feedstock Recycling of Waste Plastic," Feedstock Recycling and Pyrolysis of Waste Plastics: Converting Waste Plastics into Diesel and Other Fuels. Edited by John Scheirs. Chichester, UK: John Wiley & Sons Ltd., (2006) pp. 285-313.

Wiriyaumpaiwong, Songchai et al. "Distillation of Pyrolytic Oil Obtained from Fast Pyrolysis of Plastic Wastes," Energy Procedia (2017) 138, pp. 111-115.

Xu, Shannan et al. "Synergistic effects of catalytic co-pyrolysis of macroalgae with waste plastics," Process Safety and Environmental Protections (2020) 137, pp. 34-48.

Yang, Bing et al. "Research and Application Development of Highly Loaded Degradable Plastic Products," Suliao (2014) 43(4), pp. 39-42, with English abstract.

Zahedi, Ali Reza et al. "Unsaturated polyester resin via chemical recyclying of off-grade poly(ethylene terephthalate)," Polymer International (2009) 58, pp. 1084-1091.

Zassa, M. Della et al. "Two-steps selective thermal depolymerization of polyethylene. 1: Feasibility and effect of devolatilization heating policy," Journal of Analytical and Applied Pyrolysis (2010) 87, pp. 248-255.

Zhang, Huiyan et al. "Catalytic pyrolysis of black-liquor lignin by co-feeding with different plastics in a fluidized bed reactor," Bioresource Technology (2015) 192, pp. 68-74.

PCT Notification of Transmittal of the International Search Report and the Written Opinion of the International Searching Authority, or the Declaration, PCT/US2018/067597, Mar. 20, 2019, 15 pages.

PCT Notification of Transmittal of the International Search Report and the Written Opinion of the International Searching Authority, or the Declaration, PCT/US2019/040944, Sep. 25, 2019, 10 pages.

PCT Notification of Transmittal of the International Search Report and the Written Opinion of the International Searching Authority, or the Declaration, PCT/US2021/049790, Dec. 3, 2021, 15 pages.

Aguado, J. et al. "Feedstock recycling of polyethylene in a two-step thermo-catalytic reaction system," Journal of Analytical Applied Pyrolysis (2007) 79, pp. 415-423.

Al-Salem, S.M. et al. "The valorization of plastic solid waste (PSW) by primary to quaternary routes: From re-use to energy and chemicals," Progress in Energy and Combustion Science (2010) 36, pp. 103-129.

Angyal, Andras et al. "Petrochemical feedstock by thermal cracking of plastic waste," Journal of Analytical Applied Pyrolysis (2007) 79, pp. 409-414.

Arabiourrutia, Miriam et al. "Pyrolysis of Polyolefins in a Conical Spouted Bed Reactor: A Way to Obtain Valuable Products," Pyrolysis, Chapter 12. Rijeka, Croatia: InTech (2017) pp. 285-304.

Ashiri, Masafumi "Use of Supercritical Water as Reaction Solvent," Kagaku Sochi (1999) 41(2), pp. 31-36, with English abstract.

Aurich, H.-P. Marl "Pyrolyse, Hydrierung, Gaserzeugung," (Pyrolysis, Hydrogenation, Gasification), Kautschuk Gummi Kunststoffe (1994) 47(8), pp. 596-601, with English abstract.

Bhaskar, Thallada et al. "Thermal degradation of ABS-Br mixed with p. and catalytic debromination by iron oxide carbon composite catalyst (Fe—C)," Green Chemistry (2002) 4(6), pp. 603-606.

Datta, Janusz et al. "Thermo-Chemical Decomposition Study of Polyurethane Elastomer Through Glycerolysis Route with Using Crude and Refined Glycerine as a Transesterification Agent," Journal of Polymers and the Environment (2018) 26(1), pp. 166-174.

De la Puente, Gabriela et al. "Recycling polystyrene into fuels by means of FCC: performance of various acidic catalysts," Applied Catalysis, B: Environmental (1998) 19(3,4), pp. 305-311.

Ding, Kuan et al. "Improving hydrocarbon yield from catalytic fast co-pyrolysis of hemicellulose and plastic in the dual-catalyst bed of CaO and HZSM-5," Bioresource Technology (2018) 261, pp. 86-92.

Dobo, Zsolt et al. "Transportation fuel from plastic wastes: Production, purification and SI engine tests," Energy (2019) 189, pp. 1-9.

Ali, Mohammad Farhat et al. "The Conversion of Waste Plastics/Petroleum Residue Mixtures to Transportation Fuels," Feedstock Recycling and Pyrolysis of Waste Plastics. Edited by John Scheirs. Chichester, UK: John Wiley & Sons Ltd., (2006) pp. 363-380.

Gala, Alberto et al. "Characterization and Distillation of Pyrolysis Liquids Coming from Polyolefins Segregated of MSW for Their Use as Automotive Diesel Fuel," Energy & Fuels (2020) 34, pp. 5969-5982.

Gebauer, Manfred et al. "Olefine aus Altkunststoffen" (Olefins from waste plastics), Chemische Technik (1995) 47(4), pp. 196-199, with English abstract.

Ghosh, Pranab et al. "Dodecyl methacrylate and vinyl acetate copolymers as viscosity modifier and pour point depressant for lubricating oil," International Journal of Industrial Chemistry (2017) 8, pp. 197-205.

Hajekova, Elena et al. "Recycling of low-density polyethylene and polypropylene via copyrolysis of polyalkene oil/waxes with naphtha: product distribution and coke formation," Journal of Analytical and Applied Pyrolysis (2005) 74, (1-2), pp. 270-281.

Hofmann, U. et al. "Rohstoffrecycling—ein Weg zum Verwerten von Altkunststoffen," (Raw materials recycling—an approach to the reuse of scrap plastics) Kunststoffe (1993) 83,(4) pp. 259-263, with English abstract.

Kaminsky, W. "Recycling of mixed plastics by pyrolysis in a fluidised bed," Macromolecular Symposia (2000) 152, pp. 191-199.

Ke-Jian, Liao et al. "A Study on Three Kinds of Alcohols Esterified Copolymer of Maleic Anhydride and Olefins as Pour-Point Depressant for Diesels," Petroleum Science and Technology (1998) 16(9, 10), pp. 971-977.

Kim, Su Jin "Comparison of Dimethylformamide with Dimethylsulfoxide for Quality Improvement of Distillate Recovered from Waste Plastic Pyrolysis Oil," Processes (2020) 8(1024), pp. 1-10.

Kodera, Yoichi et al. "Continuous-Distribution Kinetic Model for Macromolecular Conversion: Asphaltene and Polymer," Preprints of Symposia—American Chemical Society, Division of Fuel Chemistry (1998) 43(3), pp. 658-662.

(56) References Cited

OTHER PUBLICATIONS

Ach, Christian "Chemical recycling: Turning plastic waste into chemical feedstock," BASF Research Press Conference Dec. 10, 2020, 9 pages.
Lange, Jean-Paul "Sustainable development: efficiency and recycling in chemicals manufacturing," Green Chemistry (2002) 4(6), pp. 546-550.
Lehner, Markus et al. "Prozesskette zum stofflichen Recycling von Kunststoffabfallen (Process Chain for the Material Recycling of Post-Consumer Plastic)," BHM (2016) 161(6), pp. 246-251, with English abstract.
Lin, Y.-H et al. "A combined kinetic and mechanistic modelling of the catalytic degradation of polymers," Journal of Molecular Catalysis A: Chemical (2001) 171(1-2), pp. 143-151.
Lin, Y.-H et al. "A novel approach for the kinetic and mechanistic modeling of acid-catalyzed degradation of polymers," Asia-Pacific Journal of Chemical Engineering (2009) 4(2), pp. 147-153.
Lin, Y.-H et al. "Catalytic conversion of commingled polymer waste into chemicals and fuels over spent FCC commercial catalyst in a fluidised-bed reactor," Applied Catalysis B: Environment (2007) 69(3-4), pp. 145-153.
Lin, Yeuh-Hui et al. "Recycling of dual hazardous wastes in a catalytic fluidizing process," Catalysis Today (2011) 174(1), pp. 37-45.
Lopez, A. et al. "Pyrolysis of municipal plastic wastes II: Influence of raw material composition under catalytic conditions," Waste Management (2011) 31, pp. 1973-1983.
Mariella, R.P. et al. "A Novel Sn1 Displacement: The Reaction of Tertiary Amines with Acetic Anhydride," Canadian Journal of Chemistry (1971) 49, pp. 3348-3351.
Meszaros, Mark W. "Advances in Plastics Recycling Thermal Depolymerization of Thermoplastic Mixtures," ACS Symposium Series (1995), 609(Plastics, Rubber, and Paper Recycling), pp. 170-182.
Miandad, R. et al. "Catalytic pyrolysis of plastic waste: A review," Process Safety and Environment Protection (2016) 102, pp. 822-838.
Miskolczi, Norbert et al. "Hydrocarbon Mixtures from Waste Polymer Degradation," Progress in Rubber, Plastics and Recycling Technology (2004) 20(1), pp. 51-68.
Miskolczi, N. et al. "Chemical Recycling of Waste Polyethylene and Polypropylene," Petroleum and Coal (2003) 45(3-4), pp. 125-130.
Missau, Juliano et al. "Development of a nanostructured filter for pyrolysis wax purification: Effects of particulate filter aids," Particuology (2021) 54, pp. 164-172.
Moinuddin, Sarker et al. "High density polyethylene (HDPE) waste plastic conversion into alternative fuel for heavy vehicles," Journal of Environmental Research and Development (2012) 7(1), pp. 1-9.
Kaminsky, W. et al. "Feedstock recycling of polymers by pyrolysis in a fluidised bed," Polymer Degradation and Stability (2004) 85(3), pp. 1045-1050.
Nishino, Junya et al. "Development of a feedstock recycling process for converting waste plastics to petrochemicals," Ishikawajima-Harima Giho (2004) 44(1), pp. 325-332.
Ondruschka, Bernd et al. "Conversion of mixtures of pyrolysis feedstocks and thermochemical pre-treated plastic wastes. An alternative of raw material plastics recycling," Chemische Technik (Leipzig) (1995) 47(4), pp. 171-179, with English abstract.
Panda, Achyut Kumar, PHD Thesis, Jul. 2011, "Studies on process optimization for production of liquid fuels from waste plastics," Department of Chemical Engineering, National Institute of Technology, Rourkela, Odisha 769008, India. 216 pages, divided into five sections.
Pasquali, Ricardo C. et al. "Some considerations about the hydrophilic-lipophilic balance system," International Journal of Pharmaceutics (2008) 356, pp. 44-51.
Pradipta, Ilham Zulfa et al. "High Grade Liquid Fuel from Plastic Waste Pyrolysis Oil by Column Distillation," 2019 IEEE Conference on Energy Conversion, Oct. 16-17, 2019 Yogyakarta, Indonesia, pp. 240-244.
Raheem, A.B. et al. "The conversion of post-consumer polyethylene terephthalate (PET) into a thermosetting polyester resin," Archives of Applied Science Research (2010) 2(4), pp. 240-254.
Sakata, Yusaku et al. "Development of a catalytic dehaologenation (Cl, Br) process for municipal waster plastic-derived oil," Journal of Material Cycles and Waste Management (2003) 5, pp. 113-124.
Sanchez-Rodriguez, Daniel et al. "Inhibition effect of amine compounds derived from hardening agents on the extraction of hydrogen bromide by water from the pyrolysis oil of brominated printed circuit boards," Journal of Cleaner Production (2020) 265, pp. 1-10.
Sarker, Moinuddin et al. "A new technology proposed to recycle waste plastics into hydrocarbon fuel in USA," International Journal of Energy and Environment (2012) 3(5), pp. 749-760.
Schleiffer, Andreas "Synthetic Crude Oil from Petroleum Waste Materials," Preprints of Papers—American Chemical Society, Division of Fuel Chemistry (1994) 39(4), pp. 1060-1064.
Serrano, D.P. et al. "Conversion of low density polyethylene into petrochemical feedstocks using a continuous screw kiln reactor," Journal of Analytical and Applied Pyrolysis (2001) 58-59, pp. 789-801.
Siddiqui, Mohammad Nahid et al. "Useful Liquid Products from the Pyrolysis of Mixed Plastics," Preprints of Papers—American Chemical Society, Division of Fuel Chemistry (2007) 52(2), pp. 761-762.
Singh, Thokchom Subhaschandra et al. "A lab scale waste to energy conversion study for pyrolysis of plastic with and without catalyst: Engine emissions testing study," Fuel (2020) 277, pp. 1-10.
Sojak, L. et al. "GC-MS of Polyethylene and Polypropylene Thermal Cracking Products," Petroleum & Coal (2006) 48(1), pp. 1-14.
Sonwane, H.W. et al. "Desulfurization of Pyrolysis Oil Obtained from Plastic Waste by Using Adsorption Method," International Research Journal of Engineering and Technology (IRJET) (2017) 4(7), pp. 1248-1251.
Srivastava, S.P, et al. "Flow Improvers and Paraffin Dispersants of Fuels," Fuels and fuel-additives (2014) pp. 243-253.
Tasheva, Yordanka et al. "Possibilities for Purification of Pyrolysis Oil to Obtain Ecological Products," Annual of Assen Zlatarov University, Burgas, Bulgaria (2011) 40, pp. 62-65.
Thahir, Ramli et al. "Production of liquid fuel from plastic waster using integrated pyrolysis method with refinery distillation bubble cap plate column," Energy Reports (2019) 5, pp. 70-77.
Al-Shafey, H.I. et al. "Studies on the Influence of Long Chain Acrylic Esters Co-Polymers Grafted With Vinyl Acetate as Flow Improver Additives of Crude Oils," Advances in Applied Science Research. 2011, 2(5) pp. 476-489.
Buekens, Alfons et al. "Technical Methods in Plastics Pyrolysis," Macromolecular Symposa. 1998, 135, pp. 63-81.
Desai, J.D. "Plastic Waste Recycling Technologies—Ecofriendly Solution," Chemical Engineering World. 1999, 34(11), pp. 73-81.
El-Gamal, I.M. et al. "Nitrogen-based copolymers as wax dispersants for paraffinic gas oils," Fuel. 1998, 77(5) pp. 375-385.
Ercole, Piero et al. "Minimizing the environmental impact of Vehicles End of Life glass recycling," Verre (Paris, France). 2008,14(1) pp. 32-38.
Krishna, R. et al. "Correlation of Pour Point of Gas Oil and Vacuum Gas Oil Fractions with Compositional Parameters," Energy & Fuels. 1989, 3(1), pp. 15-20.
Leube, Walter et al. "Wax-Crystal Modification for Fuel Oils by Self-Aggregating Partially Crystallizable Hydrocarbon Block Copolymers," Energy & Fuels. 2000, 14(2), pp. 419-430.
Montrikool, O. et al. "Effects of maleic anhydride on degradation of PVC during pyrolysis," Journal of Analytical and Applied Pyrolysis. 2005, 73, pp. 77-84.
PCT International Search Report and Written Opinion for PCT/US2022/046428, mailed Jan. 26, 2023, 17 pages.
Soldi, Rafael A. et al. "Polymethacrylates: Pour point depressants in diesel oil," European Polymer Journal. 2007, 43, pp. 3671-3678.
Song, Yuping et al. "Study on the relationship between the structure and activities of alkyl methacrylate-maleic anhydride polymers as cold flow improvers in diesel fuels," Fuel Processing Technology. 2005, 86, pp. 641-650.
Soni, Hemant P. et al. "Performance-Based Designing of Wax Crystal Growth Inhibitors.," Energy & Fuels. 2008, 22(6), pp. 3930-3939.

(56) References Cited

OTHER PUBLICATIONS

Turemuratov et al. "Synthesis and Properties of Depressators Based on Sopolymers in the Presence of Gossypol Pitch," Oriental Journal of Chemistry. 2015, 31(3) pp. 1447-1453.
Xu, Jun et al. Synthesis of Poly(maleic acid alkylamide-co-r-olefin-co-styrene) Co-polymers and Their Effect on the Yield Stress and Morphology of Waxy Gels with Asphaltenes, Energy & Fuels. 2011, 25, pp. 573-579.
Xue et al. "The influence of polymethyl acrylate as a pour point depressant for biodiesel," Energy Sources, Part A: Recovery, Utilization, and Environmental Effects. 2016, 39(1), 17-22.
Zabarnick, Steven et al. "Studies of Urea Treatment on the Low-Temperature Properties of Jet Fuel," Energy & Fuels. 2002, 16(6), pp. 1565-1570.
International Preliminary Report on Patentability for PCT/US2023/0141430, mailed Sep. 19, 2024, 13 pages.
Paramasivam Baranitharan et al: "Investigation and improvement on storage stability of pyrolysis oil obtained from Aegle marmelos de-oiled seed cake", Energy Sources, Part A: Recovery, Utilization, and Environmental Effects, vol. 43, No. 8, Jun. 24, 2019, pp. 953-967.
Sakthivel R. et al: "Experimental investigation on improvement of storage stability of bio-oil derived from intermediate pyrolysis of Calophyllum inophyllum seed cake", Journal of the Energy Institute, vol. 92, No. 3, Mar. 1, 2018, pp. 768-782.
Sharma Abhishek et al: "Effect of blending waste tyre derived fuel on oxidation stability of biodiesel and performance and emission studies of a diesel engine", Applied Thermal Engineering, Pergamon, Oxford, GB, vol. 118, Mar. 3, 2017, pp. 365-374.

\* cited by examiner

STABILIZER ADDITIVES FOR PLASTIC-DERIVED SYNTHETIC FEEDSTOCK

TECHNICAL FIELD

The application is directed at stabilizing synthetic feedstock derived from plastics.

BACKGROUND

Plastic is the fastest growing waste product and poses a significant environmental problem. Converting waste plastic into useful, higher value products such as crude oil or feedstock for the production of olefins in a steam cracker provides an opportunity to deal with the plastic waste problem.

Plastic is primarily made up of polyethylene and polypropylene. Through various processes such as pyrolysis, the carbon-carbon bonds and carbon-hydrogen bonds of the plastics are broken into shorter chains. The breakdown of the plastic can result in varying types and amounts of the oligomeric chains or monomers high in ethylene, propylene, butadiene, styrene and other unsaturates (e.g., $\alpha$-$\omega$ di-olefins which could have multiple reactive units).

The unsaturated components are inherently unstable and subject to deterioration due to oxidation or the monomers can repolymerize, which can result in gums or sediment within the plastic-derived synthetic feedstocks.

Oxidation and gums can cause problems during the recovery, transport, storage, or use of the synthetic feedstocks and fouling various process equipment leading to problems such as plugging and corrosion of the various production units. The precipitated gum-like materials can block filters, pumps, pipelines, and other installations or be deposited in tanks, thus entailing additional cleaning and costs.

BRIEF SUMMARY

Described herein are compositions and methods for improving the stability of synthetic fuels derived from plastics such as reducing gum formation or sediment of synthetic feedstocks from plastics.

In one aspect of the application is a method of stabilizing a plastic-derived synthetic feedstock composition comprising adding an antioxidant composition to a plastic-derived synthetic feedstock composition.

In another aspect of the application is a method of obtaining the synthetic feedstock comprising:
(a) heating plastic under substantially oxygen free conditions at a temperature of from about 400° C. to about 800° C. to produce a pyrolysis effluent;
(b) distilling the pyrolysis effluent;
(c) recovering the synthetic feedstock; and
(d) adding a stabilizer to the synthetic feedstock to reduce contamination.

In still another aspect of the application is a composition comprising a synthetic feedstock derived from plastic and an antioxidant.

In another aspect of the application is a composition comprising an antioxidant and a synthetic feedstock, wherein the antioxidant is added to the synthetic feedstock, the synthetic feedstock is provided by the method comprising:
(a) heating plastic under substantially oxygen free conditions at a temperature from about 400° C. to about 800° C. to produce a pyrolysis effluent;
(b) distilling the pyrolysis;
(c) condensing or quenching the pyrolysis effluent from distillation to provide the synthetic feedstock; and
(d) adding the antioxidant to the synthetic feedstock after the step of condensing.

The stabilizer composition and method are used to prevent or reduce oxidation of polymers, formation of gum or residue, discoloration or combinations thereof during recovery, transport, storage or use of the synthetic feedstocks derived from plastics.

BRIEF DESCRIPTION OF THE DRAWING FIGURES

DETAILED DESCRIPTION

Figure 1:
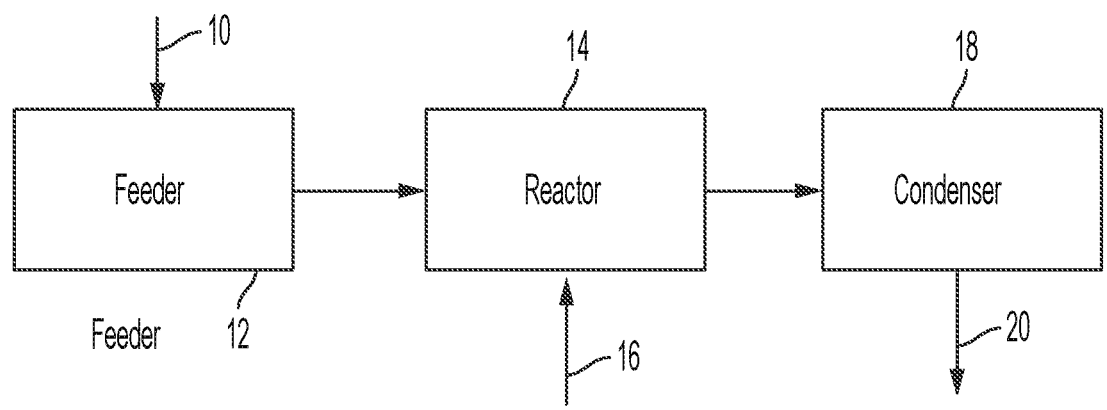
FIG. 1 is a schematic representation of an embodiment of a plastic pyrolysis process.

Although the present disclosure provides references to various embodiments, one of ordinary skill in the art will recognize that changes may be made in form and detail without departing from the spirit and scope of the application. Various embodiments will be described in detail with reference to the figures. Reference to various embodiments does not limit the scope of the claims attached hereto. Additionally, any examples set forth in this application are not intended to be limiting and merely set forth some of the many possible embodiments for the appended claims.

Unless otherwise defined, all technical and scientific terms used herein have the same meaning as commonly understood by one of ordinary skill in the art. In case of conflict, the present document, including definitions, will control. Methods and materials are described below, although methods and materials similar or equivalent to those described herein can be used in practice or testing of the present application. All publications, patent applications, patents and other references mentioned herein are incorporated by reference in their entirety.

The term "antioxidant" as used herein is a compound that can inhibit, prevent or reduce oxidation, deterioration, degradation and gum formation. Antioxidants are capable of acting as scavengers preventing free radical formation.

As used herein, the term "process equipment" means compressors, inter-coolers, sensors, condensers, quench towers and the like that are associated with the process and which may be subject to fouling. This term also includes sets of components which are in fluidic or gas communication.

The term "stabilizer" as used herein refers to a composition that prevents or reduces discoloration of the synthetic feedstock, prevents or reduces the formation or settling out of insoluble products (e.g., gums) or combinations thereof.

The term "synthetic feedstock" refers to hydrocarbons obtained from treatment or processes on plastics such as thermochemical conversion of plastics.

As used herein, the terms "comprise(s)," "include(s)," "having," "has," "can," "contain(s)," and variants thereof are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "optional" or "optionally" means that the subsequently described event or circumstance may but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. In some embodiments, "about" may refer to, for example, within 5% of the cited value.

As used herein, the term "substantially" means "consisting essentially of" and includes "consisting of" "Consisting essentially of" and "consisting of" are construed as in U.S. patent law. For example, a solution that is "substantially free" of a specified compound or material may be free of that compound or material, or may have a minor amount of that compound or material present, such as through unintended contamination, side reactions, or incomplete purification. A "minor amount" may be a trace, an unmeasurable amount, an amount that does not interfere with a value or property, or some other amount as provided in context. A composition that has "substantially only" a provided list of components may consist of only those components, or have a trace amount of some other component present, or have one or more additional components that do not materially affect the properties of the composition. Additionally, "substantially" modifying, for example, the type or quantity of an ingredient in a composition, a property, a measurable quantity, a method, a value, or a range, employed in describing the embodiments of the disclosure, refers to a variation that does not affect the overall recited composition, property, quantity, method, value, or range thereof in a manner that negates an intended composition, property, quantity, method, value, or range. Where modified by the term "substantially" the claims appended hereto include equivalents according to this definition.

As used herein, any recited ranges of values contemplate all values within the range and are to be construed as support for claims reciting any sub-ranges having endpoints which are real number values within the recited range. By way of example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

Described are compositions and methods that stabilize synthetic feedstocks derived from plastics and thereby improve the synthetic feedstock quality. The stability of the synthetic feedstock can be improved by additives that inhibit, prevent or reduce gum formation, discoloration and oxidation. In some embodiments, stability is achieved by use of antioxidants.

Several processes are known in which plastic (e.g., waste plastic) is converted to lower molecular weight hydrocarbon materials particularly to hydrocarbon fuel materials. For example, see U.S. Pat. Nos. 6,150,577; 9,200,207; and 9,624,439; each of these publications incorporated herein by reference in their entireties. Such processes broadly described include breaking the long-chain plastic polymers by thermochemical conversion such as pyrolysis—high heat (e.g., from about 400° C. to about 850° C.) with limited or no oxygen and above atmospheric pressure. Pyrolysis conditions include temperatures from about 500 to about 700° C. The resultant pyrolysis effluent is distilled and then condensed.

Figure 2:
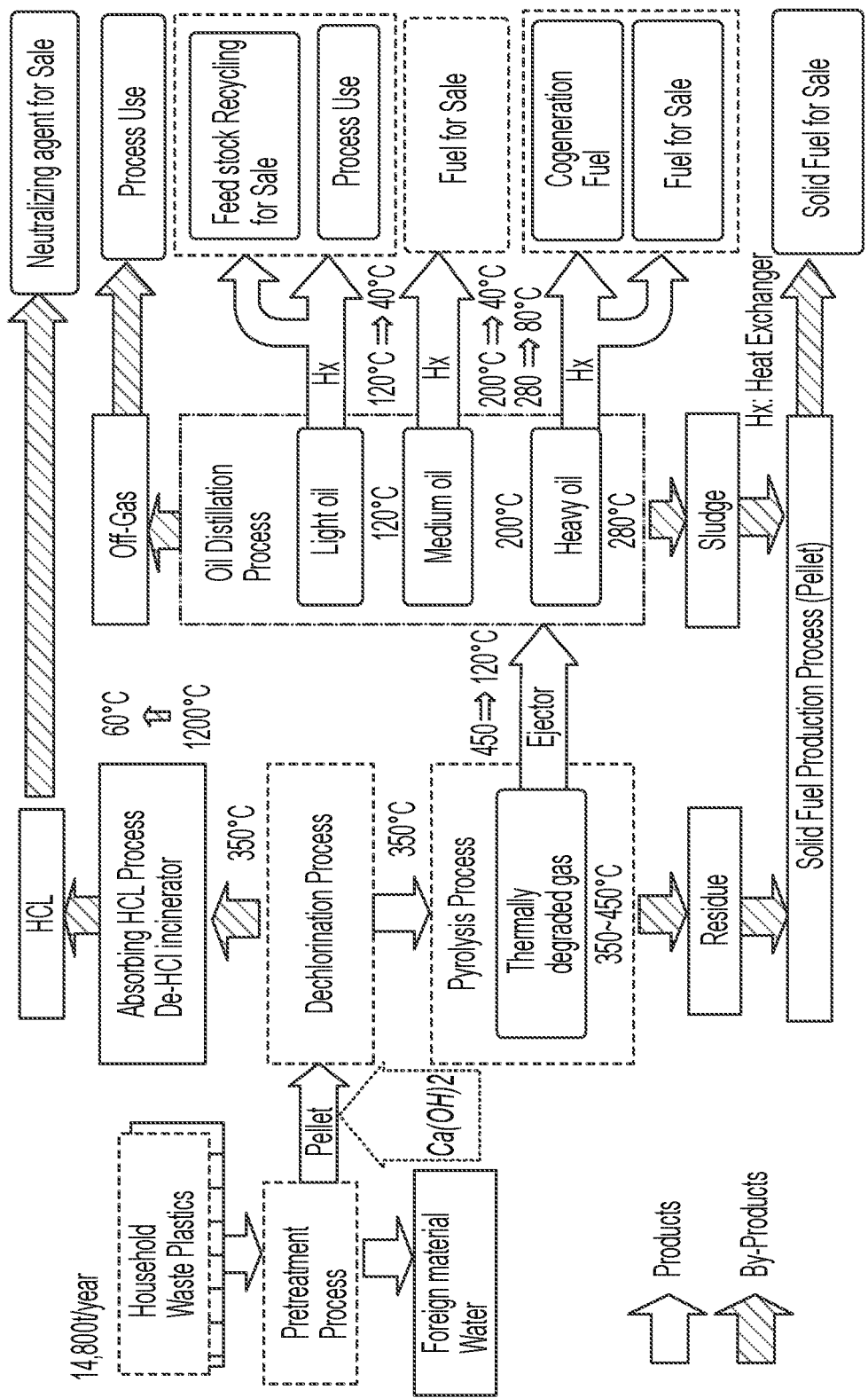
FIG. 2 is a schematic representation of an embodiment of a plastic pyrolysis process.
Figure 3:
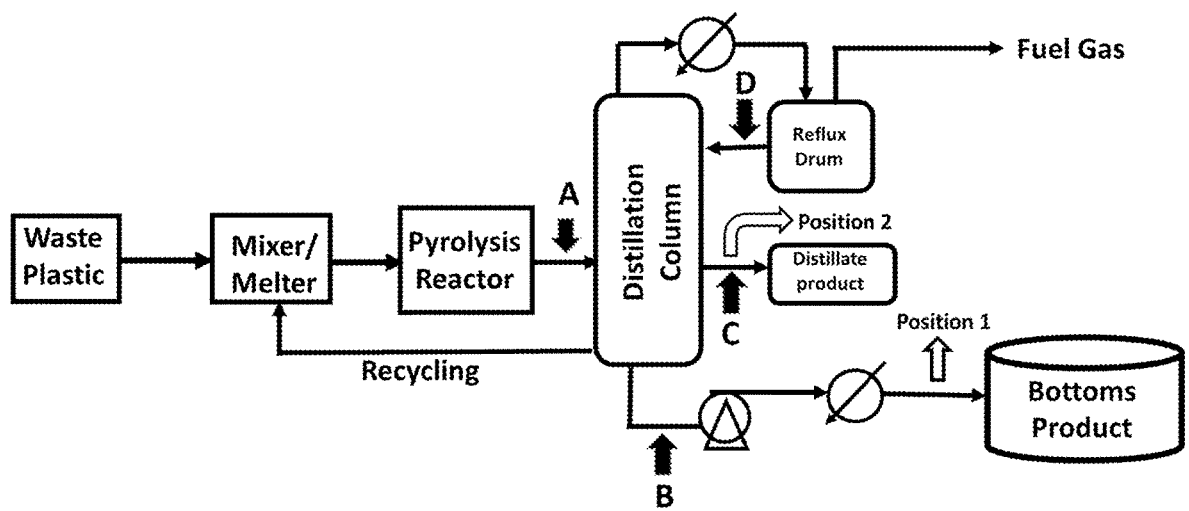
FIG. 3 is a schematic representation of an embodiment of a plastic pyrolysis process showing the treatment with a stabilizer composition and collection of samples after treatment.

As shown in FIG. 1, an embodiment of a pyrolysis process includes a feeder 12 of waste plastic, a reactor 14, and a condenser system 18. Polymer-containing material is fed through inlet 10 in the feeder, and heat is applied to reactor 14. An outlet 20 from condenser system 18 allows for the product to exit. FIG. 2 depicts another embodiment of a pyrolysis process for plastic. FIG. 3 depicts yet another embodiment showing a process for the condensing or quenching and collection of the pyrolysis effluent.

The thermal cracking reactors to accomplish this pyrolysis reaction have been described in detail in a number of patents, e.g., U.S. Pat. Nos. 9,624,439; 10,131,847; 10,208,253; and PCT International Patent Application Publication No. WO 2013/123377A1, each of these publications incorporated herein by reference in their entireties. In some embodiments, the method of obtaining the synthetic feedstock is in the presence or absence of catalysts.

In some embodiments, the method of obtaining the synthetic feedstock comprises:
(a) heating plastic under substantially oxygen free conditions at a temperature from about 400° C. to about 800° C. to produce a pyrolysis effluent;
(b) distilling the pyrolysis effluent to obtain the synthetic feedstock;
(c) recovering synthetic feedstock; and
(d) adding a stabilizer additive to the synthetic feedstock to stabilize the synthetic feedstock.

In some embodiments, recovering synthetic feedstock relates to separating or quenching or both the pyrolysis effluent to obtain the synthetic feedstock. In some embodiments, the stabilizer additive is added to the synthetic feedstock after the feedstock exits the quenching column. In some embodiments, the stabilizer additive is added at Positions A, B, C, D, or any combination thereof, as shown in FIG. 3.

The pyrolysis reaction produces a range of hydrocarbon products from gases (at temperatures from about 10° C. to about 50° C. and about 0.5 to about 1.5 atmospheric pressure and having 5 carbons or less); modest boiling point liquids (like gasoline (about 40 to about 200° C.) or diesel fuel (about 180 to about 360° C.)); a higher (e.g., about 250 to about 475° C.) boiling point liquid (oils and waxes), and some solid residues, commonly referred to as char. Char is the material that is left once the pyrolytic process is complete and the fuel recovered. Char contains the additives and contaminants that enter the system as part of the feedstock. The char can be a powdery residue or substance that is more like sludge with a heavy oil component. Glass, metal, calcium carbonate/oxide, clay and carbon black are just a few of the contaminants and additives that will remain after the conversion process is complete and become part of the char.

Various plastic types such a thermoplastic or thermoplastic waste can be used in the above described process. The types of plastics commonly encountered in waste-plastic feedstock include, without limitation, low-density polyethylene, high-density polyethylene, polypropylene, polystyrene and the like, and combinations thereof.

In some embodiments, the pyrolysis of plastic results in synthetic feedstocks that include about 2 to about 30 wt. % gas ($C_1$-$C_4$ hydrocarbon); about 10 to about 50 wt. % oil ($C_5$-$C_{15}$ hydrocarbon); about 10 to about 40 wt. % waxes ($\geq C_{16}$ hydrocarbon); and about 1 to about 5 wt. % char and tar.

The hydrocarbons that derive from the pyrolysis of waste plastic are a mixture of alkanes, alkenes, olefins and diolefins; the olefin group is generally between $C_1$ and $C_2$, viz. alpha-olefin, some alk-2-ene is also produced; the diene is generally in the alpha and omega position, viz. alk-α,ω-diene. In some embodiments, the pyrolysis of plastic produces paraffin compounds, isoparaffins, olefins, diolefins, naphthenes and aromatics. In some embodiments, the percentage of 1-olefins in the pyrolysis effluent is from about 25 to about 75 wt. %; or from about 35 to about 65 wt. %.

Depending on the processing conditions synthetic feedstock can have characteristics similar to crude oil from petroleum sources but may have varying amounts of olefins and diolefins. In some embodiments, the synthetic feedstock derived from waste plastic contains about 35 to about 65 wt. % olefins and/or diolefins, about 10 to about 50 wt. % paraffins and/or iso-paraffins, about 5 to about 25 wt. % naphthenes, and about 5 to about 35 wt. % aromatics. In some embodiments, the synthetic feedstocks have about 15 to about 20 wt. % $C_9$-$C_{16}$; about 75 to about 87 wt. % $C_{16}$-$C_{29}$; about 2 to about 5 wt. % $C_{30+}$, where the carbon chains are predominantly a mixture of alkanes, alkenes and diolefins. In other embodiments, the synthetic feedstocks have about 10 wt. %<$C_{12}$, about 25 wt. % $C_{12}$-$C_{20}$, about 30 wt. % $C_{21}$-$C_{40}$ and about 35 wt. %>$C_{41}$ where the carbon chains are predominantly a mixture of alkanes, alkenes and diolefins.

In some embodiments, the synthetic feedstock composition has a range of alpha or omega olefins monomer constituents which can precipitate from the synthetic feedstock composition at a temperature greater than its desired or intended during storage, transport, or use temperature. In some embodiments, the synthetic feedstock is about 25 to about 70 wt. % olefins and diolefins; about 35 to about 65 wt. %; from about 35 to about 60 wt. %; or about 5 to about 50 wt. % olefins and/or diolefins.

The stabilizer compositions include one or more compounds that can work against, for example, ethylenically unsaturated monomers reducing contamination, which in turn inhibits, prevents or reduces gum formation and discoloration or both of the synthetic feedstock. In some embodiments the stabilizer composition comprises antioxidants. In some embodiments, the antioxidant is phenolic, an aromatic amine or mixtures and combinations thereof. Examples of antioxidants include phenolic antioxidants, such as hindered phenols and phenylenediamines thereof to prevent oxidation and unwanted polymerization (e.g., radical) of ethylenically unsaturated monomers.

In some embodiments, the phenolic antioxidant is a hindered phenol. In some embodiments, hindered phenol is an alkylated phenolic antioxidant. In some embodiments, the antioxidant is a hindered phenol including alkyl-substituted hindered phenols and aromatic amines or mixtures and combinations thereof. In some embodiments, the phenol is a butyl substituted phenol containing 2 or 3 t-butyl groups.

In some embodiments, the hindered phenols are generally alkyl phenols of the formula:

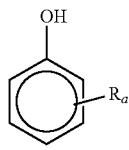

wherein $R_a$ is independently an alkyl group containing from 1 up to about 24 carbon atoms and a is an integer of from 1 up to 5, 1 to 4, 1 to 3 or 1 to 2. In some embodiments, $R_a$ contains from 4 to 18 carbon atoms, or from 4 to 12 carbon atoms. $R_a$ may be either straight chained or branched chained. In some embodiments, the hindered phenolic antioxidant is an alkyl phenol selected from ter-butyl, OH, $OCH_3$ methylphenyl or mixtures thereof.

In some embodiments, the hindered phenol is 2-tert-butylphenol, 4-tert-butylphenol 2,4-di-tert-butylphenol, 2,6-di-tert-butylphenol, 2,4, 6-tri-tert-butylphenol, 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,6-di-tert-butyl-4-methoxyphenol, 2,5-di-tert-butylhydroquinone, 2,5-di-tert-amylhydroquinone, 2,6-diphenyl-4octadecyloxyphenol, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 2,2'-methylenebis(6-tert-butyl-4-methylphenol), 2,2'-methylenebis(6-tert-butyl-4-ethylphenol), 2,2'-methylenebis 4-methyl-6-(α-methylcyclohexyl)phenol, 2,2'-methylenebis (4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis 6-(α-methylbenzyl)-4-nonylphenol, 2,2'-methylenebis 6-(α,α-dimethylbenzyl)-4-nonylphenol, 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis 3,3-bis(3'-tert-butyl-4'-hydroxyphenyl) butyrate, bis(3-tert-butyl-4-hydroxy-5-methylphenyl)dicyclopentadiene, bis 2-(3'-tert-butyl-2'-hydroxy-5'-methylbenzyl)-6-tert-butyl-4-methylphenylterephthalate, 1,3,5-tris(3, 5-di-tert-butyl-4-hydroxybenzyl)-2,4,6-trimethylbenzene, bis(3,5-di-tert-butyl-4-hydroxybenzyl)sulfide, isooctyl 3,5-di-tert-butyl-4-hydroxybenzylmercaptoacetate, bis(4-tert-butyl-3-hydroxy-2,6-dimethylbenzyl) dithioterephthalate, 1,3,5-tris(3,5-di-tert-butyl-4-hydroxybenzyl) isocyanurate, 1,3,5-tris(4-tert-butyl-3-hydroxy-2,6-dimethylbenzyl)isocyanurate, dioctadecyl 3,5-di-tert-butyl-4-hydroxybenzylphosphonate and the calcium salt of monoethyl 3,5-di-tert-butyl-4-hydroxybenzylphosphonate or a tert-butylcatechol.

In some embodiments, the antioxidant is an aromatic amine. In some embodiments, the antioxidant is an alkylated phenylenediamine, which can include an unsubstituted phenylenediamine, N-substituted phenylenediamine or N,N'-substituted phenylenediamine targeted towards an ethylenically unsaturated monomer, and any combination thereof. Examples of phenylenediamine are 1,4-phenylenediamine, N,N'-dimethyl-p-phenylenediamine, N, N'-di-sec-butyl-p-phenylenediamine, N, N'-di-sec-butyl-1,4-phenylenediamine, N-phenyl-N'-dibutyl-p-phenylenediamine, N-phenyl-N'-(1,4-dimethylphenyl)-p-phenylenediamine, N-phenyl-N'-(1,3-dimethylbutyl)-p-phenylenediamine, and any combination thereof. Phenylenediamines can also include p- or m-phenylenediamine itself (PDA); N,N'-diphenyl-p-phenylenediamine; N,N,N',N'-tetramethyl-p-phenylenediamine; N,N'-bis-(1,4-dimethylpentyl)-phenylenediamine; N-phenyl-N'-(1,4-dimethylpentyl) p-phenylenediamine; N-phenyl-N'-(1,3-dimethylbutyl) p-phenylenediamine; N-phenyl-N-cyclohexyl p-phenylenediamine; N,N'-dinaphthyl p-phenylenediamine; N-isopropyl-N'-phenyl p-phenylenediamine; N-aminoalkyl-N'-phenyl p-phenylenediamine; N-(2-methyl-2-aminopropyl)-N'-phenyl p-phenylenediamine; phenyl-b-isopropyl-aminophenylamine;p-hydroxydiphenylamine;p-hydroxylphenyl-b-naphthylamine; 1,8-naphthalenediamine.

Hindered phenolic compounds can include o- and p-sec-butylphenol; 2,4-di-sec-butylphenol; 2,6-di-sec-butylphenol; 2,4,6-tri-sec-butylphenol; 2,4,6-trimethylphenol; butylated hydroxytoluene (BHT, also known as 2,6-tert-butyl-4-methylphenol and 2,6-tert-butyl p-cresol); 2,6-dibutyl-4-methylphenol; hydroquinone; monomethylether of hydroquinone (MEHQ); 2,6-bis (1,6 dimethylethyl-4-(1-methylpropyl) phenol), b-naphthoquinone; N-phenyl p-aminophenol; and combinations thereof. In some embodiments, the stabilizer composition comprises 2-tert-butylphenol, 4-tert-butylphenol 2,4-di-tert-butylphenol, 2,6-di-tert-butylphenol, 2,4, 6-tri-tert-butylphenol, 1,2,4-trimethyl benzene, N, N'-di-sec-butyl-1,4-phenylenediamine or combinations thereof.

In some embodiments, the antioxidant or blend thereof is present at about 0.1 wt. % to about 100 wt. %, 0.1 wt. % to about 50 wt. %, or about 1 wt. % to about 50 wt. %, about 1 wt. % to about 30 wt. %, about 1 wt. % to about 20 wt. %, about 1 wt. % to about 10 wt. %, about 2 wt. % to about 30 wt. %, about 2 wt. % to about 20 wt. %, about 2 wt. % to about 10 wt. %, about 50 wt. % to about 100 wt. %, about 60 wt. % to about 100 wt. %; about 50 wt. % to about 90 wt. % of the stabilizer composition. In some embodiments, the stabilizer composition comprises, consists essentially of or consists of the formulations shown in Tables 1 and 2.

The stabilizer compositions can include one or more solvents. Suitable solvents include any solvent in which combinations of the antioxidants are soluble or dispersible. In some embodiments, the solvents are hydrophobic solvents such as aromatic solvents, paraffinic solvents. Examples of hydrophobic solvents include heavy aromatic naphtha, toluene, ethylbenzene, and isomeric hexanes, and mixtures thereof.

The concentration of one or more solvents in the stabilizer composition is not particularly limited. In some embodiments, the concentration of one or more solvents can be about 10 wt. % to about 50 wt. %, about 20 wt. % to about 50 wt. %, about 30 wt. % to about 50 wt. %, about 10 wt. % to about 40 wt. %, about 10 wt. % to about 30 wt. %, about 20 wt. % to about 40 wt. %, or about 30 wt. % to about 40 wt. % of the stabilizer composition.

The stabilizer composition can include other additives that include other antioxidants, paraffin inhibitors, asphaltene dispersants, wax dispersants, tar dispersants, neutralizers, surfactants, biocides, preservatives, or any combination thereof.

While the amount of stabilizer composition (e.g., antioxidant) used depends on a number of factors, such as the type of plastic used, the type of contamination, the local operating conditions, examples of amounts introduced into process equipment containing a synthetic feedstock stream through either injection into the feed stream or direct injection to each compression stage (e.g., as shown in Position A, B, C, and/or D from FIG. 3) range from about 1 ppm to about 5,000 ppm of the combination of the stabilizer composition, such as from about 5 ppm to about 4,000 ppm, about 5 ppm to about 3,000 ppm, about 5 ppm to about 2,000 ppm, about 5 ppm to about 1,000 ppm, about 1 ppm to about 500 ppm, about 10 ppm to about 500 ppm, about 20 ppm to about 500 ppm, about 30 ppm to about 500 ppm, about 40 ppm to about 500 ppm, about 50 ppm to about 500 ppm, about 60 ppm to about 500 ppm, about 70 ppm to about 500 ppm, about 80 ppm to about 500 ppm, about 90 ppm to about 500 ppm, about 100 ppm to about 500 ppm, about 5 ppm to about 450 ppm, about 5 ppm to about 400 ppm, about 5 ppm to about 350 ppm, about 5 ppm to about 300 ppm, about 5 ppm to about 250 ppm, about 5 ppm to about 200 ppm, about 5 ppm to about 150 ppm, about 5 ppm to about 100 ppm, about 10 ppm to about 300 ppm, about 10 ppm to about 250 ppm, about 50 ppm to about 250 ppm, or about 50 ppm to about 200 ppm, based on the stabilizer compositions.

The stabilizer compositions are useful in preventing or reducing deposition of polymers and in some cases preventing or reducing polymer formation in process equipment, such as quench towers or columns used in synthetic feedstock production processes. The stabilizer composition may be added at one or more locations in a process. In some embodiments, the stabilizer composition can be added directly at an inlet of a quench tower or distillation column as shown in FIG. 3 denoted by the letter "A", the outlet of the distillation column, or inlet to the bottoms product or a surge drum as shown in FIG. 3 and denoted by the letter "B" or combination thereof. In some embodiments, some of these inlets can be located before or pass through other equipment & machinery, such as chiller units and/or filtration skids. In some embodiments, the stabilizer composition can be added directly after a distillation column as denoted by the letter "C" in FIG. 3 and/or after a reflux drum as denoted by the letter "D" re-entering the distillation column as shown in FIG. 3. The stabilizer composition can be added to any combination of locations A, B, C and D. In some embodiments, the stabilizer composition is added at the outlet of the quenching tower or the distillation column when the synthetic feed stock vapor leaving a pyrolysis reactor is quenched and the gases are cooled and condensed at a temperature from about 150° C. to about 200° C. or about 160° C. to about 180° C. In some embodiments, the stabilizer composition is added to a synthetic feedstock held in storage. The stabilizer composition can be added continuously or intermittently to the process equipment as required.

The stabilizer composition may be added by any suitable method. For example, the stabilizer composition may be added in neat or a dilute solution. In some embodiments, the stabilizer composition may be applied as a solution, emulsion, or dispersion that is sprayed, dripped, poured or injected into a desired opening within a system or onto the process equipment or the fluid contained therein. In some embodiments, the stabilizer composition can be pumped or injected into a system in a continuous fashion or as a high volume flush to clean the system.

The stabilizer composition is applied to a process equipment to form a treated process equipment. In some embodiments, treated process equipment can be observed to undergo less polymer deposition on process equipment than on process equipment without addition of the stabilizer composition. Reduction or prevention in the polymer formation or polymer deposition can be evaluated by any known method or test. Stabilization of the synthetic feedstock can also be evaluated measuring the contamination amounts according to EN 12662, ASTM D2274, or ASTM D 4625. Color can be evaluated by ASTM D1500. Further, the Applicant discovered that a modified version of the Rancimat method may be used to determine oxidative stability as well.

In some embodiments, the synthetic feedstocks with the stabilizer additive have contamination reduced by about 5% to about 95%; about 5% to about 75%; about 5% to about 50%; about 5% to about 25%; about 5% to about 15%; about 50% to about 95%; about 50% to about 20%; or about 50% to about 75%.

In some embodiments, the synthetic feedstocks with the stabilizer additive have contamination reduced by about 5% to about 95%; about 5% to about 75%; about 5% to about 50%; about 5% to about 25%; about 5% to about 15%; about 50% to about 95%; about 50% to about 20%; or about 50% to about 75%, as measured under EN 12662. In some embodiments, color of the synthetic feedstock is lightened compared to synthetic feedstock without the addition of the stabilizer composition.

In some embodiments, the stabilizer is an antioxidant. In some embodiments, the stabilizer is added into a synthetic feedstock obtained from plastics. In some embodiments, the stabilizer composition comprises, consists essentially of, or consists of 2-tert-butylphenol, 4-tert-butylphenol, 2,4-di-tert-butylphenol, 2,6-di-tert-butylphenol, 2,4, 6-tri-tert-butylphenol, 1, 2, 4-trimethyl benzene, N,N'-di-sec-butylphenylene diamine or combinations thereof that is added to synthetic feedstock obtained from plastics. In other embodiments, the stabilizer composition is added to a synthetic feedstock that contains varying amounts of monomers.

In some embodiments, the 2-tert-butylphenol, 4-tert-butylphenol, 2,4-di-tert-butylphenol, 2,6-di-tert-butylphenol, 2,4, 6-tri-tert-butylphenol, 1, 2, 4-trimethyl benzene, N,N'-di-sec-butylphenylene diamine or combinations thereof are added to a synthetic feedstock that contains about 35 to about 65 wt. % olefins and/or diolefns.

In some embodiments, the N,N'-di-sec-butylphenylene diamine, 2,6-di-tert-butylphenol, 2,4-di-tert-butylphenol, 2,4,6-tri-tert-butylphenol, 2-tert-butylphenol, 4-tert-butylphenol, or combinations thereof are added to synthetic feedstock obtained after quenching and having about 35 wt. % to about 65 wt. % olefins and/or diolefins, about 10 wt. % to about 50 wt. % paraffins and/or iso-paraffins, about 5 wt. % to about 25 wt. % naphthenes, and about 5 wt. % to about 35 wt. % aromatics, where the carbon chains are predominantly a mixture of alkanes, alkenes and diolefins.

In still other embodiments, 2,6-di-tert-butylphenol, 2,4-di-tert-butylphenol, 2,4,6-tri-tert-butylphenol, 2-tert-butylphenol, 4-tert-butylphenol, or combinations thereof are added to synthetic feedstock having about 35 wt. % to about 65 wt. % olefins and/or diolefins, about 10 wt. % to about 50 wt. % paraffins and/or iso-paraffins, about 5 wt. % to about 25 wt. % naphthenes, and about 5 wt. % to about 35 wt. % aromatics.

EXAMPLES

The following examples are intended to illustrate different aspects and embodiments of the invention and are not to be considered limiting the scope of the invention. Some of the following examples are prophetic while others have already been conducted. It will be recognized that various modifications and changes may be made without departing from the scope of the claims.

Example 1: Stabilization Additives in Synthetic Feedstock Derived from Plastic

The effect of stabilization additives on synthetic feedstocks derived from plastic will be determined by the insoluble material that it contains. This will be evaluated by the Total Contamination test according to EN12662, or another substantially equivalent or similar test, and color according to ASTM D1500.

Stabilization Additive 1 or Stabilization Additive 2 will be added into the feedstock stream at the inlets of a distillation column at its operating temperature, such as from about 130° C. to about 190° C., as shown in FIG. 3 at Positions A & D, and/or at the outlets of a distillation column at its operating temperatures and shown in FIG. 3 at Positions B & C, and based on the flow rate of the feedstock stream will be added at a concentration of approximately 50-500 ppm until a steady state is achieved. A blank sample (no additive) will also be evaluated.

The compositions of the stabilization additives are shown in Table 1 and Table 2.

TABLE 1

| Stabilization Additive 1 | |
|---|---|
| Component | Wt % |
| 2,6-di-tert-butylphenol | 61-80 |
| Heavy aromatic naptha | 14-17 |
| 2,4-di-tert-butylphenol | 8-12 |
| 2,4,6-tri-tert-butylphenol | 5-8 |
| Naphthalene | 1-3 |
| 2-tert-butylphenol | 1-2 |
| 1,2,4-trimethylbenzene | 1-2 |
| Ethylbenzene | 0.0001-0.0002 |

TABLE 2

| Stabilization Additive 2 | |
|---|---|
| Component | Wt % |
| N,N'-di-sec-butylphenylene diamine | 50-60 |
| 2,6-di-tert-butylphenol | 35-40 |
| 2,4-di-tert-butylphenol | 3-8 |
| 2,4,6-tri-tert-butylphenol | 3-6 |
| 2-tert-butylphenol | 0.5-1.5 |

TABLE 3

Stabilization Additive 3

| Component | Wt % |
|---|---|
| N,N'-di-sec-butylphenylenediamine | 50 |
| Kerosene | 50 |

The stabilization additives will be added into a feedstock stream having about 35-65% olefins and/or diolefins, about 10-50% paraffins and/or iso-paraffins, about 5-25% naphthenes, and about 5-35% aromatics.

Samples will be collected each day for several consecutive days at multiple locations in the process stream, such as Positions 1 & 2 as shown in FIG. 3, or directly from various pyrolysate product collection/storage containers including bottoms product, distillate product, and reflux drums as shown in FIG. 3.

We believe the data will show that each of the two additives tested will reduce gum formation. We also believe that Stabilization Additive 1 will produce a sample synthetic feedstock of a lighter appearance with visually less residue.

Example 2: Variation in Stabilization Additive Concentration in Synthetic Feedstock Derived from Plastic Increasing concentrations of Stabilization Additive 1 (as described in Example 1) will be added into the flow stream of synthetic feedstocks derived from plastic at an outlet of a distillation column at its operating temperatures, such as from about 130° C. to about 190° C., and based on the flow rate of the feedstock stream at increasing concentrations (from about 50 to about 700 ppm) every day over multiple days.

As described in Example 1, total contamination concentration will be determined according to EN12662, or a substantially equivalent or similar test method, and color according to ASTM D1500, and samples will be collected at Position 1 and 2 as described in Example 1.

In Examples 3-6, the effect of stabilization/antioxidant additives to enhance the thermo-oxidative stability of a wide range of pyrolysis oils (obtained from different suppliers) was quantitatively demonstrated by a modified version of the Rancimat method.

According to the modified version of the Rancimat method carried out by the inventors, a stream of purified air is passed through the pyrolysis oil sample, which is heated to a specified temperature. These isothermal thermo-oxidative conditions result in the oxidation of the sample. Volatile reaction/oxidation products are formed, which are transported into the measuring vessel by the airstream and absorbed into the measuring solution (deionized water). The electrical conductivity of the measuring solution increases due to the absorption of the reaction/oxidation products. The time until a sharp increase in the conductivity occurs is called induction time. Oxidative stability is expressed as "induction time," and longer induction times correspond to higher oxidative stability.

Example 3: Stabilization of a Pyrolysis Oil by Treatment with Antioxidant Additives This example shows the relative efficacy of various antioxidants at a treat rate of about 500 ppm in improving the thermo-oxidative stability of a pyrolysis oil. The induction time (IT) determinations were made at about 150° C. and about 10 L/h of air.

TABLE 4

| Sample Description | Induction time (h) measured at 150° C. |
|---|---|
| Blank (No AO)-Supplier 1 | 4.47 |
| 2,6-Di-tert-butylphenol | 11.64 |
| Stabilization Additive 1 | 14.12 |
| Stabilization Additive 3 | 15.25 |
| Stabilization Additive 2 | 19.60 |
| 2,6-Di-t-butyl-4-(dimethylaminomethyl)phenol | 5.40 |
| Irganox ® L-57 | 4.66 |
| t-Butylcatechol | 7.33 |

Among the tested antioxidants, the Stabilization Additive 3 was the best performer whereas Irganox® L-57 was the worst performer as it provided an insignificant increase in induction time compared to the untreated pyrolysis oil.

Example 4: Enhanced Stabilization of a Pyrolysis Oil by Increasing the Concentration of an Antioxidant (Antioxidant Performance Vs Concentration Effect)

The examples (4a and 4b) demonstrate that the thermo-oxidative stability of pyrolysis oils can be improved to different extents by increasing the concentration of an antioxidant additive. The results are provided in the tables provided below.

Example 4a: Effect of concentration of Stabilization Additive 1 on the performance at about 140° C., about 10 L/h air for a pyrolysis oil from Supplier 2.

TABLE 5

| Sample Description | Conc. (ppm) | Induction time (h) measured at 140° C. |
|---|---|---|
| Blank (No AO)-Supplier 2 | 0 | 2.28 |
| Stabilization Additive 1 | 250 | 3.91 |
| Stabilization Additive 1 | 500 | 6.60 |
| Stabilization Additive 1 | 1000 | 12.6 |

Example 4b: Effect of concentration of Stabilization Additive 3 on the performance at about 150° C., about 10 L/h air for a pyrolysis oil from Supplier 3.

TABLE 6

| Sample Description | Conc. (ppm) | Induction time (h) measured at 150° C. |
|---|---|---|
| Blank (No AO)-Supplier 3 | 0 | 4.97 |
| Stabilization Additive 3 | 100 | 8.37 |
| Stabilization Additive 3 | 250 | 10.94 |
| Stabilization Additive 3 | 500 | 15.25 |

Example 5: Stabilization of a Pyrolysis Oil Having Very Poor Oxidative Stability This example demonstrates the effect of stabilization/antioxidant additives in substantially improving the thermo-oxidative stability of a pyrolysis oil having very poor baseline oxidative stability. The results are provided in the table provided below. This pyrolysis oil, without any antioxidant added to it, had poor stability as indicated by a very low OSI value (about 0.31 h at about 130° C., about 10 L/h air).

TABLE 7

Performance of different antioxidants at about
130° C. for a pyrolysis oil from Supplier 4

| Sample Description | Conc. (ppm) | Induction time (h) measured at 130° C. |
|---|---|---|
| Blank (Untreated)-Supplier 4 | 0 | 0.31 |
| Stabilization Additive 1 | 500 | 0.72 |
| Stabilization Additive 3 | 500 | 2.71 |
| Stabilization Additive 2 | 500 | 3.17 |

Of the tested additives, Stabilization Additive 2 and Stabilization Additive 3, at a treat rate of about 500 ppm, caused a significant increase (9-10 times) in the induction time for this feedstock.

Example 6: Stabilization of a Waxy Plastics Pyrolysate

This example shows the relative efficacy of antioxidants in improving the thermo-oxidative stability of a waxy plastics pyrolysate. This waxy pyrolysate (which was a solid at room temperature) was first melted at about 80° C. and then treated with different antioxidant additives. The induction time (IT) determinations were made at about 150° C. and about 10 L/h of air.

TABLE 8

Performance of different antioxidants at about
150° C. for a waxy pyrolysate from Supplier 5

| | IT (h) measured at 150° C. | |
|---|---|---|
| Sample Description | 250 ppm | 500 ppm |
| Blank (Untreated)-Supplier 5 | 7.12 | 7.12 |
| Stabilization Additive 1 | 8.78 | 10.42 |
| Stabilization Additive 3 | 14.63 | 21.38 |
| Stabilization Additive 2 | 14.56 | 20.85 |

At a treat rate of about 250 ppm, both Stabilization Additive 2 and Stabilization Additive 3 doubled the induction time, when compared with untreated pyrolysis oil. At a treat rate of about 500 ppm, these two additives increased the induction time by almost three times.

Any composition disclosed herein may comprise, consist of, or consist essentially of any element, component and/or ingredient disclosed herein or any combination of two or more of the elements, components or ingredients disclosed herein.

Any method disclosed herein may comprise, consist of, or consist essentially of any method step disclosed herein or any combination of two or more of the method steps disclosed herein.

Unless specified otherwise, all molecular weights referred to herein are weight average molecular weights and all viscosities were measured at 25° C. with neat (not diluted) polymers.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method of stabilizing a plastic-derived synthetic feedstock composition comprising:
    heating plastic in a pyrolysis reactor to produce a plastic-derived synthetic feedstock composition,
    distilling the plastic-derived synthetic feedstock composition in a distillation column, and
    adding an antioxidant composition to the plastic-derived synthetic feedstock composition, wherein the adding is before any distilling in any distillation column, and
    wherein the adding is at an outlet of the pyrolysis reactor, an inlet of a quenching tower, and/or an inlet of the distillation column wherein the synthetic feedstock comprises about 2 wt. % to about 30 wt. % gas ($C_1$-$C_4$ hydrocarbon); (2) about 10 wt. % to about 50 wt. % oil ($C_5$-$C_{15}$ hydrocarbon); (3) about 10 wt. % to about 40 wt. % waxes ($\geq C_{16}$ hydrocarbon); and (4) about 1 wt. % to about 5 wt. % char and tar.

2. The method of claim 1, wherein the synthetic feedstock comprises about 35 wt. % to about 65 wt. % olefins and/or diolefins, about 10 wt. % to about 50 wt. % paraffins and/or iso-paraffins, about 5 wt. % to about 25 wt. % naphthenes, and about 5 wt. % to about 35 wt. % aromatics.

3. The method of claim 1, wherein the antioxidant comprises an alkylated phenol, an aromatic diamine, or any combination thereof.

4. The method of claim 3, wherein the alkylated phenol comprises 2-tert-butylphenol, 4-tert-butylphenol 2,4-di-tert-butylphenol, 2,6-di-tert-butylphenol, 2,4,6-tri-tert-butylphenol, or any combination thereof.

5. The method of claim 3, wherein the aromatic diamine comprises a phenylenediamine.

6. The method of claim 1, wherein the synthetic feedstock composition further comprises other stabilizers and antioxidants, paraffin inhibitors, asphaltene dispersants, wax dispersants, tar dispersants, neutralizers, surfactants, biocides, preservatives, or any combination thereof.

7. The method of claim 1, wherein the antioxidant is added to the synthetic feedstock composition from about 1 ppm to 5,000 ppm.

8. The method of claim 1, wherein the antioxidant composition comprises an alkylated phenol and an aromatic diamine.

* * * * *